United States Patent
Hsu

(10) Patent No.: US 6,749,299 B1
(45) Date of Patent: Jun. 15, 2004

(54) AUXILIARY FRAME FOR EYEGLASSES

(75) Inventor: Wan-Ting Hsu, Tainan (TW)

(73) Assignee: Sun Sight Glasses Co., Ltd., Tainan (TW)

( * ) Notice: Subject to any disclaimer, the term of this patent is extended or adjusted under 35 U.S.C. 154(b) by 0 days.

(21) Appl. No.: 10/654,317

(22) Filed: Sep. 3, 2003

(51) Int. Cl.⁷ .............................................. G02C 11/08
(52) U.S. Cl. ................ 351/62; 351/47; 2/435
(58) Field of Search ........................... 351/62, 47, 57, 351/44, 41, 158; 2/435

(56) References Cited

U.S. PATENT DOCUMENTS 6,062,688 A * 5/2000 Vinas ........................... 351/47
6,641,263 B2 * 11/2003 Olney .......................... 351/62

* cited by examiner

*Primary Examiner*—Hung X. Dang
(74) *Attorney, Agent, or Firm*—Alan D. Kamrath; Nikolai & Mersereau, P.A.

(57) ABSTRACT

A flexible, auxiliary frame mounted on a flexible frame of a pair of eyeglasses is disclosed. The frame includes, at its back, a hole in a center of a bridge, two protrusions having a larger bottom at both sides of the hole, and two slots at endpieces. The auxiliary frame comprises a forward tab at a bridge, two grooves at both sides of the tab, two projections having a larger outer end disposed at endpieces, and a rear pad. The projections are matingly fitted in the slots, the tab is fitted in the hole, and the protrusions are fitted in the grooves respectively. Further, the frame together with the auxiliary frame are adapted to flexibly expand with the fastening of the projections in the slots being maintained in response to the wearer's larger head.

2 Claims, 6 Drawing Sheets

AUXILIARY FRAME FOR EYEGLASSES

BACKGROUND OF THE INVENTION

1. Field of the Invention

The present invention relates to eyeglasses and more particularly to an improved auxiliary frame releasably mounted on the frame of a pair of sunglasses or the like.

2. Description of Related Art

Conventionally, a wearer of sunglasses likes to mount an auxiliary frame on the frame of the sunglasses. The auxiliary frame typically has a pad on the back for providing a degree of comfort to the wearer and/or protection. A conventional such auxiliary frame 30 is shown in FIGS. 1 and 2. As illustrated, a pair of lenses 101 are supported in a frame 10 of a pair of sunglasses 40. The frame 10 further comprises, at its back, two holes 103 at both sides of bridge 102 and two substantially parallelepiped slots 104 each at an endpiece coupled to a pivotable temple 20. Correspondingly, the auxiliary frame 30 comprises two forward tabs 301 at both sides of bridge, two substantially parallelepiped projections 302 each at an endpiece, and a pad at its back. Each of the frame 10 and the auxiliary frame 30 is formed of thermoplastic material so as to be bendable. The auxiliary frame 30 is mounted on the frame 10 with the projections 302 snugly fitted in the slots 104 and the tabs 301 snugly fitted in the holes 103 respectively (see circles D and E of FIG. 2).

Advantageously, the auxiliary frame 30 can be removed from the frame 10 for storage in an unused state. Also, such assembly is adapted to fit different individuals with various head sizes. For example, as shown in FIG. 3, in a case of the wearer having a larger head, the frame 10 flexibly, laterally expands in response thereto. Unfortunately, this may result in a partial or even complete withdrawal of the projections 302 from the slots 104 due to the substantially parallelogramic shapes of the projections 302 and the slots 104 and in turn the forming of a gap 50 at either endpiece between the frame 10 and the auxiliary frame 30 (see circle F). Such gaps 50 will inevitably loosen the whole eyeglasses 40. Thus, the need for improvement still exists.

SUMMARY OF THE INVENTION

It is an object of the present invention to provide a flexible, auxiliary frame mounted on a flexible frame of a pair of eyeglasses, the frame including, at its back, a hole in a center of a bridge, two protrusions having a larger bottom at both sides of the hole, and two slots at endpieces, the auxiliary frame comprising a forward tab at a bridge thereof; two grooves at both sides of the tab; two projections having a larger outer end disposed at endpieces thereof; and a rear pad, wherein the projections are matingly fitted in the slots, the tab is fitted in the hole, and the protrusions are fitted in the grooves respectively, and the frame together with the auxiliary frame are adapted to flexibly expand in response to a lateral bending.

In one aspect of the present invention each of the frame and the auxiliary frame is formed of thermoplastic material.

The above and other objects, features and advantages of the present invention will become apparent from the following detailed description taken with the accompanying drawings.

DETAILED DESCRIPTION OF THE PREFERRED EMBODIMENTS

Figure 1:
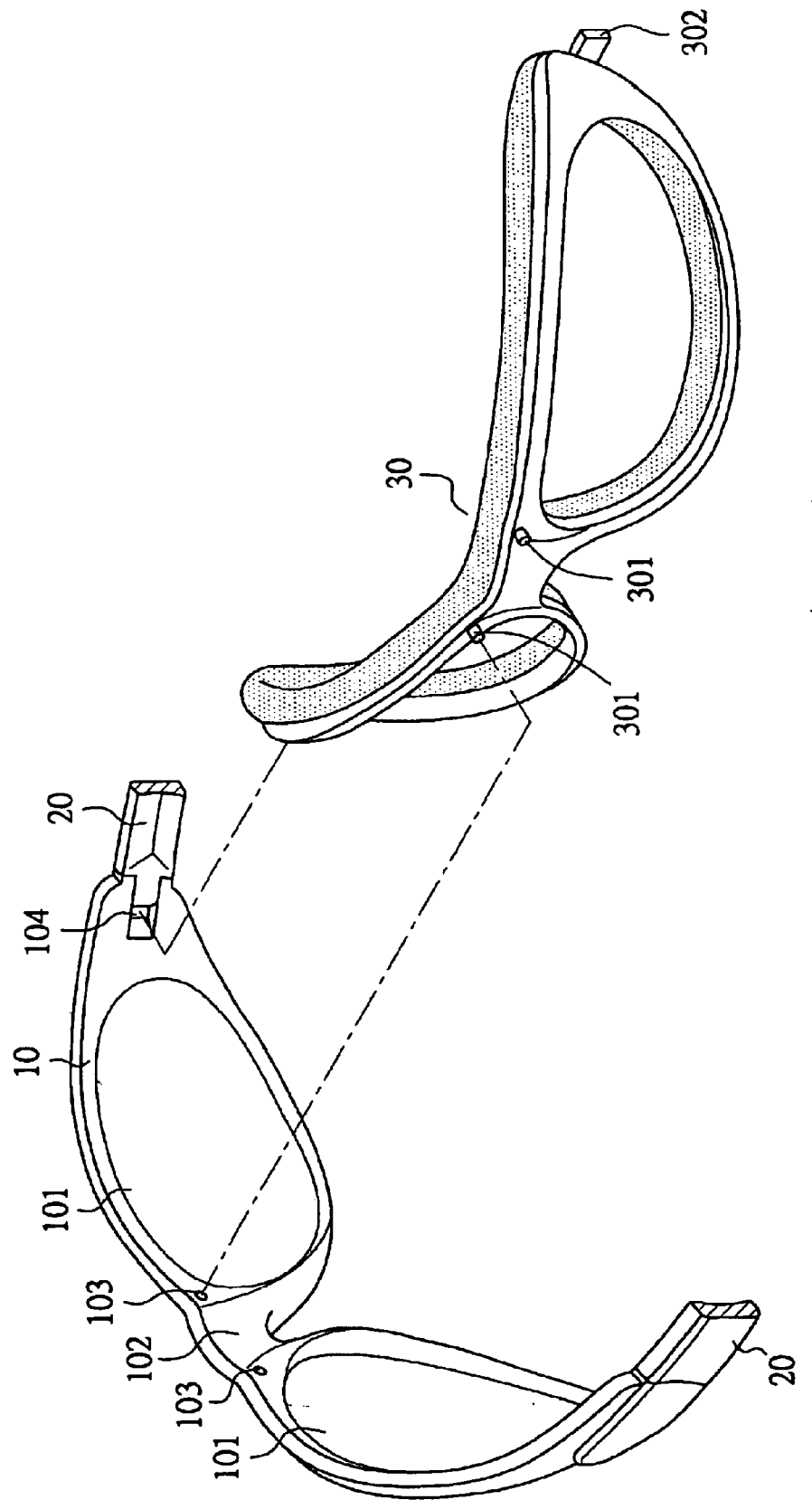
FIG. 1 is a perspective view of a conventional auxiliary frame to be mounted on the frame of a pair of eyeglasses.
Figure 2:
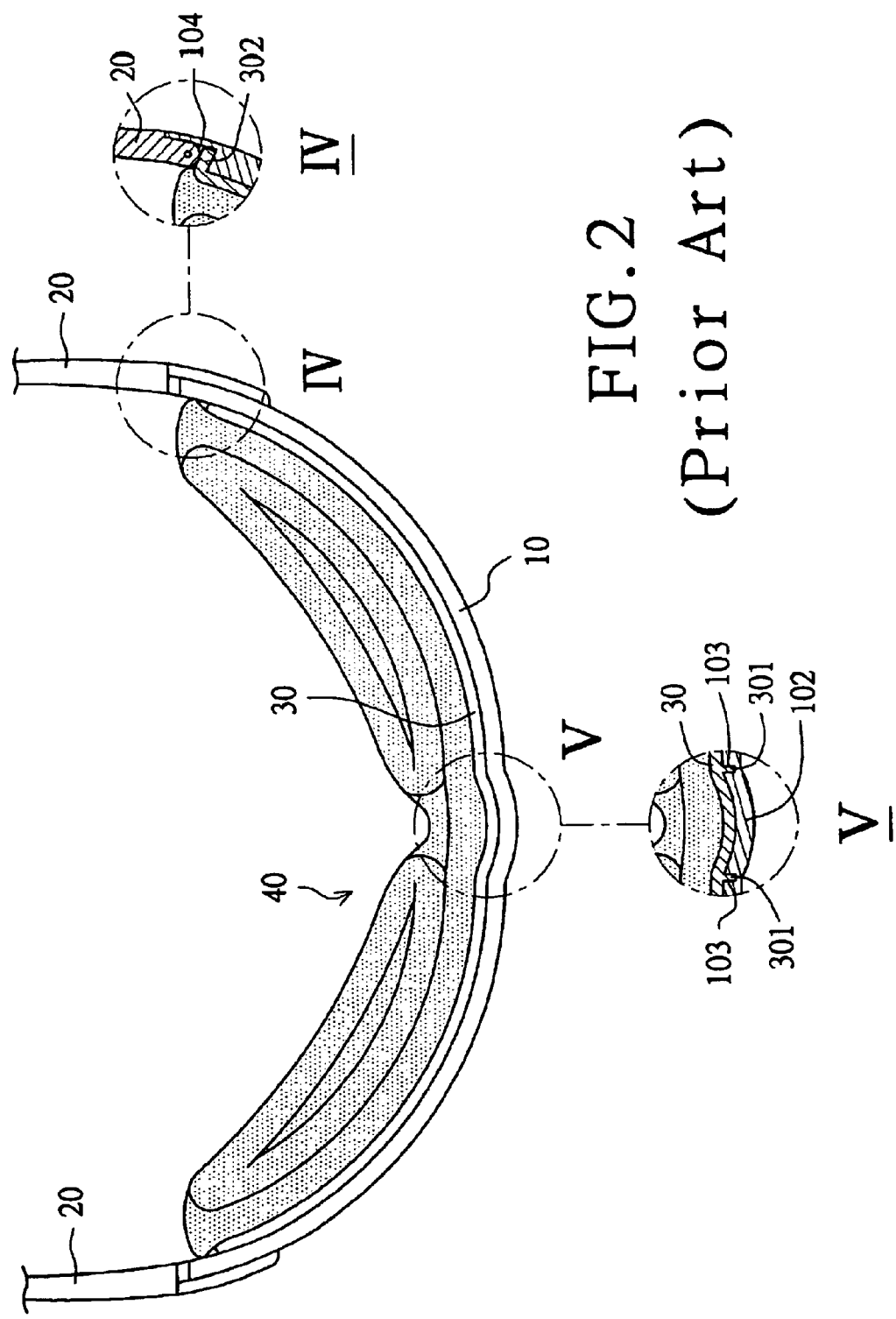
FIG. 2 is top plan view of the assembled auxiliary frame and the eyeglasses with details of the fastening of the projection in the slot and the tabs in the holes shown in circles D and E respectively.
Figure 3:
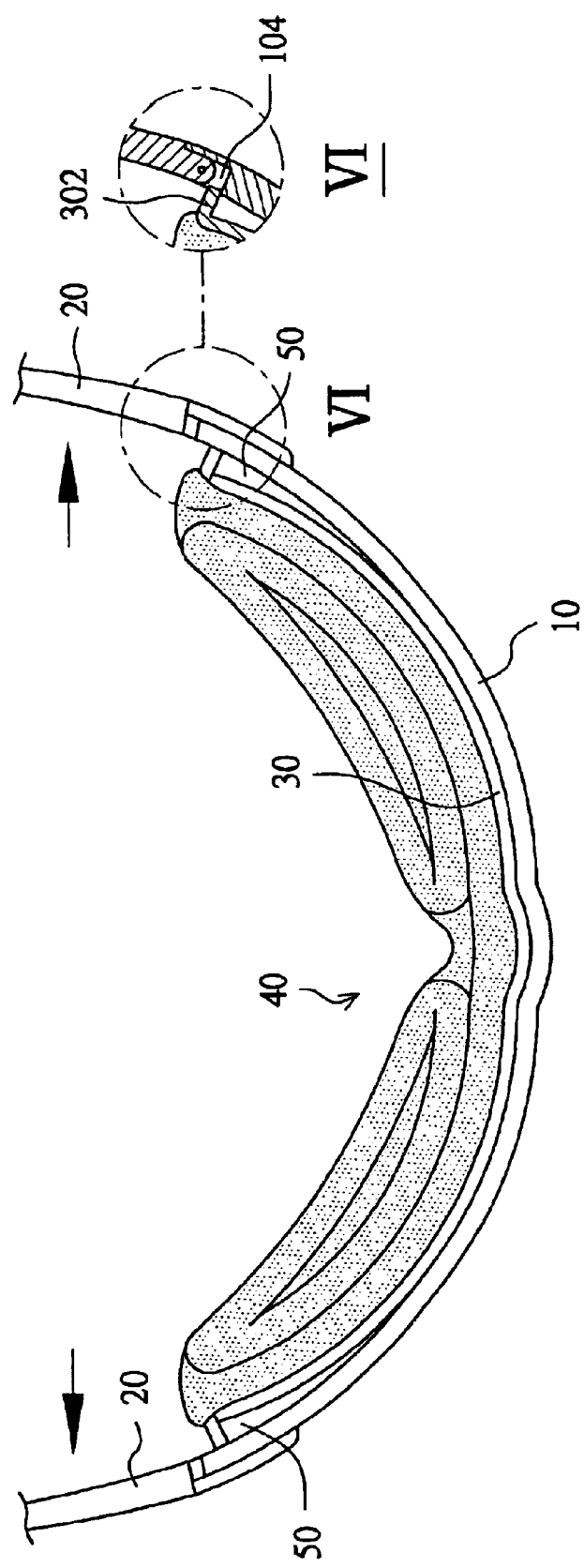
FIG. 3 is a view similar to FIG. 2, where a gap is formed between the frame of the eyeglasses and the auxiliary frame and details of a substantially complete withdrawal of the projection from the slot is shown in a circle F due to the larger head of the wearer.
Figure 4:
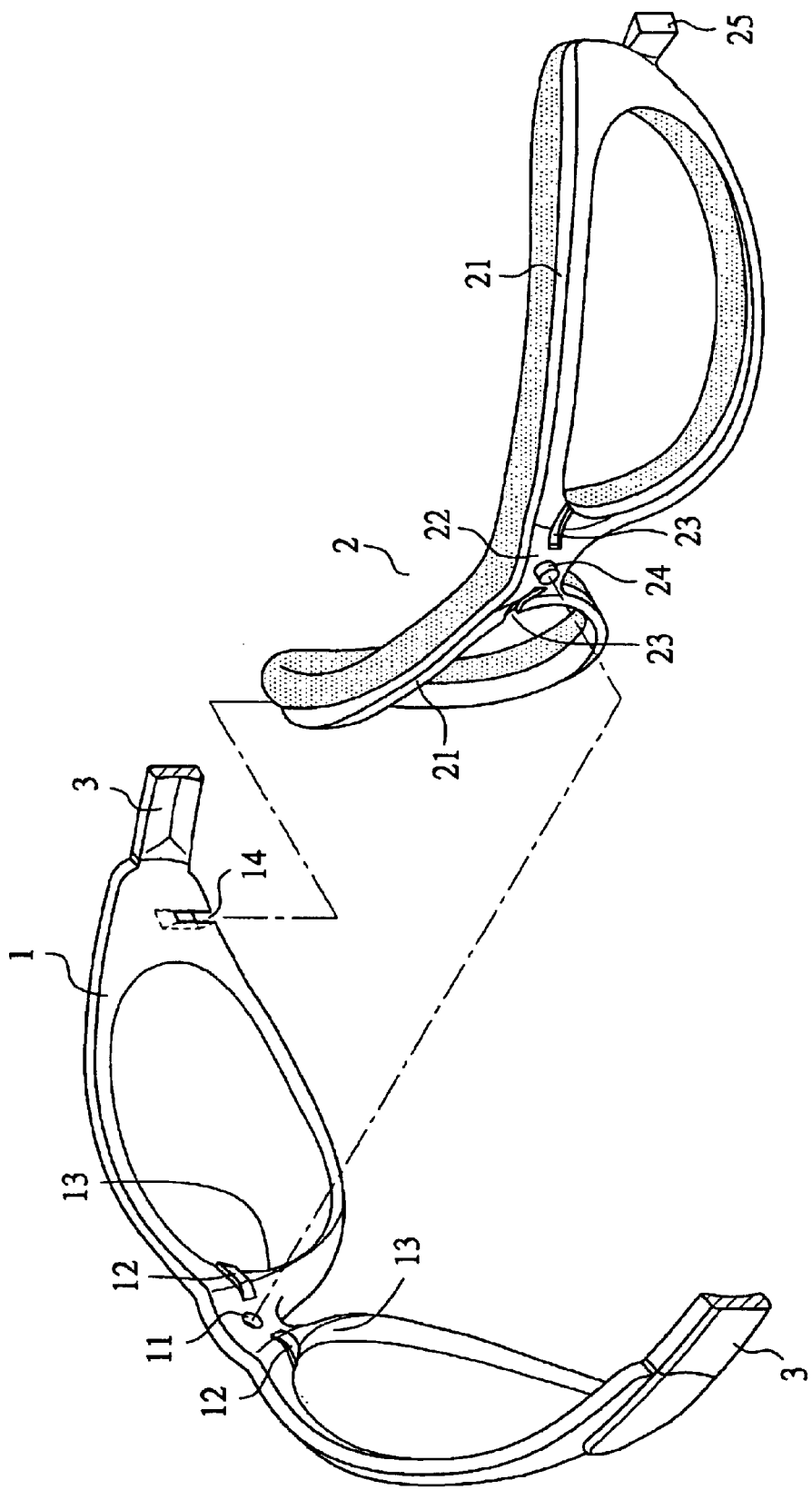
FIG. 4 is a perspective view of an auxiliary frame according to the invention to be mounted on the frame of a pair of eyeglasses.
Figure 5:
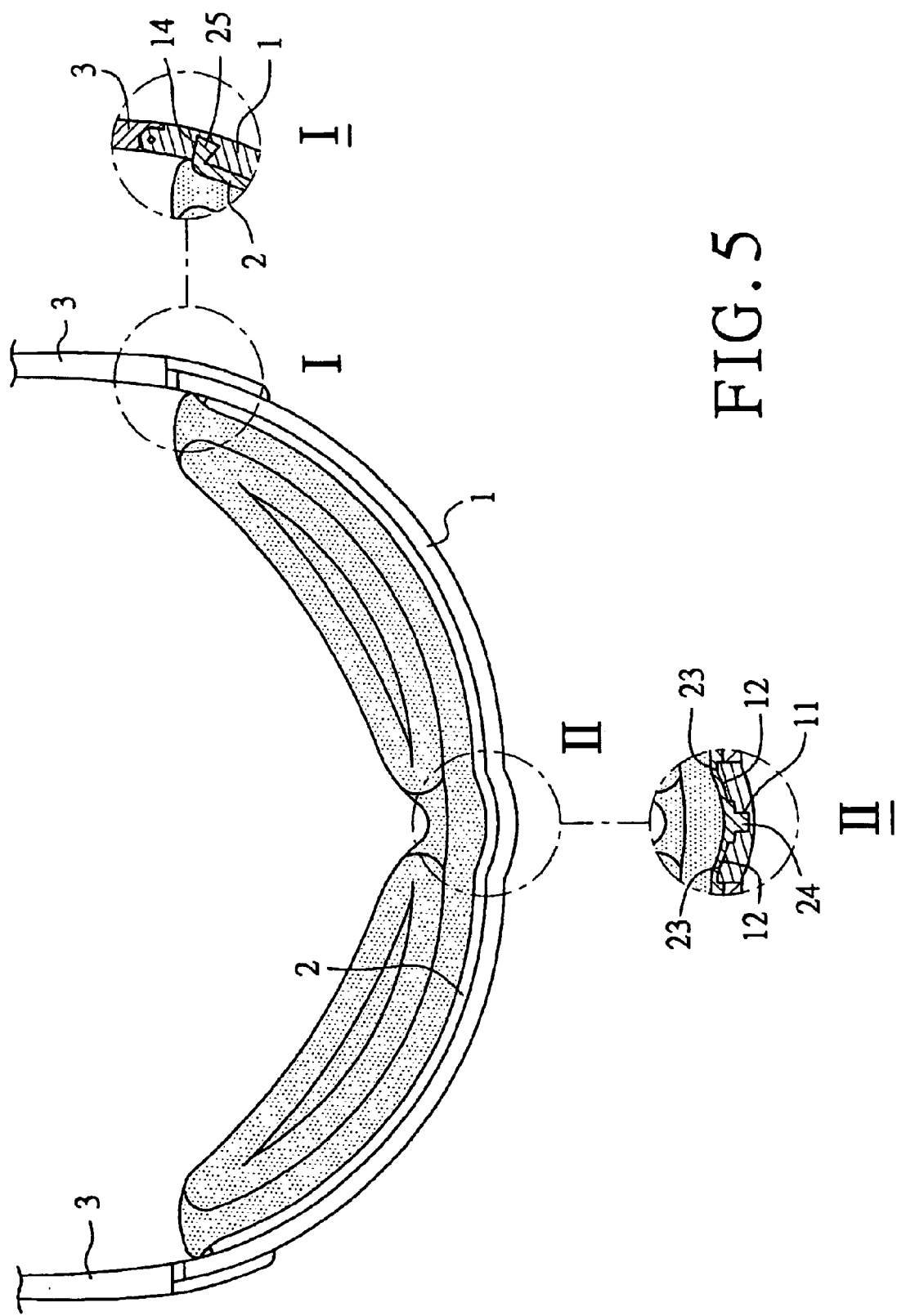
FIG. 5 is top plan view of the assembled auxiliary frame and the eyeglasses with details of the fastening of the projection in the slot as well as the tab in the hole and the protrusions in the grooves shown in circles A and B respectively.

Referring to FIGS. 4 and 5, there is shown an auxiliary frame 2 constructed in accordance with the invention. As illustrated, a pair of lenses 11 are supported in a frame 1 of a pair of sunglasses. Each of the frame 1 and the auxiliary frame 2 is formed of thermoplastic material so as to be bendable. The frame 1 further comprises, at its back, a hole 11 in a center of bridge, two protrusions 12 having a larger bottom disposed at both sides of the hole 11, the protrusions 12 being flush with two nosepads 13, and two slots 14 each at an endpiece coupled to a pivotable temple 3. The auxiliary frame 2 comprises left and right frame elements 21. Correspondingly, the auxiliary frame 2 further comprises a forward tab 24 at a bridge 22, two grooves 23 at both sides of the bridge 22, two projections 25 having a larger outer end each disposed at an endpiece, and a pad at its back. The auxiliary frame 2 is mounted on the frame 1 with the projections 25 matingly, snugly fitted in the slots 14, the tab 24 snugly fitted in the hole 11, and the protrusions 12 snugly fitted in the grooves 23 respectively (see circles A and B of FIG. 5).

Figure 6:
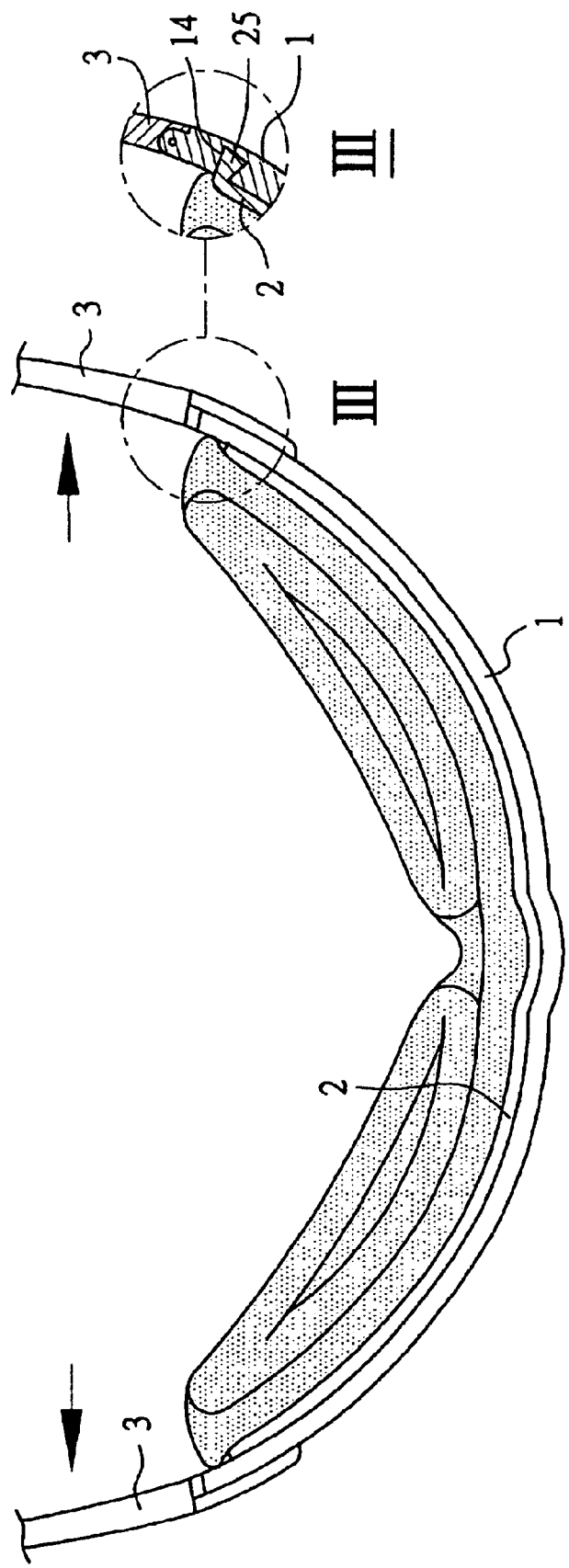
FIG. 6 is a view similar to FIG. 5, where details of the fastening of the projection in the slot is shown in a circle C in which the fastening is not compromised even the wearer has a larger head.

Advantageously, the auxiliary frame 2 can be removed from the frame 1 for storage in an unused state. Also, such assembly is adapted to fit different individuals with various head sizes. For example, as shown in FIG. 6, in a case of the wearer having a larger head, both the frame 1 and the auxiliary frame 2 flexibly, laterally expand in response thereto with no gap formed therebetween. This is because even a partial withdrawal of the projections 25 from the slots 14 is prohibited by the mated shapes of the projections 25 and the slots 14 (see circle C). More advantageously, the fastening can be maintained even during violent or repeated movement of the wearer's head.

While the invention herein disclosed has been described by means of specific embodiments, numerous modifications and variations could be made thereto by those skilled in the art without departing from the scope and spirit of the invention set forth in the claims.

What is claimed is:

1. A flexible, auxiliary frame mounted on a flexible frame of a pair of eyeglasses, the frame including, at its back, a hole in a center of a bridge, two protrusions having a larger bottom at both sides of the hole, and two slots at endpieces, the auxiliary frame comprising:

a forward tab at a bridge thereof;

two grooves at both sides of the tab;

two projections having a larger outer end disposed at endpieces thereof; and a rear pad, wherein the projections are matingly fitted in the slots, the tab is fitted in the hole, and the protrusions are fitted in the grooves respectively, and the frame together with the auxiliary frame are adapted to flexibly expand in response to a lateral bending.

2. The auxiliary frame of claim 1, wherein each of the frame and the auxiliary frame is formed of thermoplastic material.

* * * * *